US012433783B2

(12) United States Patent
Watson

(10) Patent No.: US 12,433,783 B2
(45) Date of Patent: Oct. 7, 2025

(54) EXTERNAL FEMALE GRAVITY-BASED DRAINAGE

(71) Applicant: C. R. Bard, Inc., Franklin Lakes, NJ (US)

(72) Inventor: Kristin Louise Watson, Social Circle, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 17/850,444

(22) Filed: Jun. 27, 2022

(65) Prior Publication Data

US 2023/0023781 A1 Jan. 26, 2023

Related U.S. Application Data

(60) Provisional application No. 63/221,784, filed on Jul. 14, 2021.

(51) Int. Cl.
*A61F 5/455* (2006.01)
*B65B 69/00* (2006.01)

(52) U.S. Cl.
CPC ........ *A61F 5/4556* (2013.01); *B65B 69/0016* (2013.01)

(58) Field of Classification Search
CPC ........ A61F 5/455; A61F 5/4556; A61F 5/451; B65B 69/0016
See application file for complete search history.

(56) References Cited

U.S. PATENT DOCUMENTS 1,113,561 A 10/1914 Jorgenson
1,241,652 A 10/1917 Norquist
4,106,490 A 8/1978 Spilman et al.
(Continued)

FOREIGN PATENT DOCUMENTS

CN 106510930 A 3/2017
CN 212369143 U 1/2021
(Continued)

OTHER PUBLICATIONS

Dictionary.com. (Sep. 9, 2017). Spheroid definition meaning. Dictionary.com. https://www.dictionary.com/browse/spheroid (Year: 2017).*
(Continued)

*Primary Examiner* — Rebecca E Eisenberg
*Assistant Examiner* — Matthew Wrubleski
(74) *Attorney, Agent, or Firm* — Rutan & Tucker LLP

(57) ABSTRACT

Embodiments described herein are directed to an external, female, gravity-based drainage system. The system includes a body having a front side and a rear side and a drainage tube extending from a bottom side. The body can include a finger groove disposed on the front side and configured to allow a user to grasp the body from the front side alone without any opposing force applied to the rear side. The user can then position the funnel, disposed on the rear side of the body, over a labia region to capture any fluids voided therefrom. The fluids can be directed towards the lumen of the drainage tube and directed towards a suitable receptacle. Advantageously, the shape of the drainage system can be easily grasped and manipulated from a single side which can be important for patients with limited manual dexterity.

25 Claims, 6 Drawing Sheets

(56) References Cited

U.S. PATENT DOCUMENTS

| | | | |
|---|---|---|---|
| 4,202,058 A | 5/1980 | Anderson | |
| 4,305,161 A | 12/1981 | Diaz | |
| 4,784,654 A | 11/1988 | Beecher | |
| 5,002,541 A | 3/1991 | Conkling et al. | |
| 5,091,998 A * | 3/1992 | Witzke | A61F 5/4556 141/333 |
| 6,332,878 B1 | 12/2001 | Wray et al. | |
| 7,181,781 B1 | 2/2007 | Trabold et al. | |
| 8,690,847 B2 | 4/2014 | Norman | |
| 8,795,248 B2 | 8/2014 | Shihata | |
| 10,226,376 B2 | 3/2019 | Sanchez et al. | |
| D898,190 S | 10/2020 | Cohn et al. | |
| 10,898,367 B2 | 1/2021 | Nelson | |
| 2003/0195483 A1* | 10/2003 | Ching | A61F 5/4556 604/327 |
| 2006/0149195 A1* | 7/2006 | Oprandi | A61F 5/4556 604/329 |
| 2009/0182296 A1 | 7/2009 | Dennis et al. | |
| 2009/0204092 A1 | 8/2009 | Loyd et al. | |
| 2009/0254040 A1 | 10/2009 | Bierman et al. | |
| 2011/0040271 A1* | 2/2011 | Rogers | A61F 5/4556 604/346 |
| 2011/0054426 A1* | 3/2011 | Stewart | A61F 5/4556 604/347 |
| 2012/0103347 A1 | 5/2012 | Wheaton et al. | |
| 2013/0218112 A1 | 8/2013 | Thompson | |
| 2015/0135423 A1* | 5/2015 | Sharpe | A61F 5/455 4/471 |
| 2015/0366699 A1* | 12/2015 | Nelson | A61G 9/006 604/329 |
| 2016/0317698 A1 | 11/2016 | Berryman et al. | |
| 2016/0374848 A1 | 12/2016 | Sanchez et al. | |
| 2017/0035600 A1* | 2/2017 | Preciado | A61F 5/4556 |
| 2018/0228642 A1 | 8/2018 | Davis et al. | |
| 2019/0038451 A1 | 2/2019 | Harvie | |
| 2019/0224036 A1 | 7/2019 | Sanchez et al. | |
| 2022/0031290 A1* | 2/2022 | Weed | A61B 10/007 |
| 2022/0152352 A1* | 5/2022 | Hughett, Sr. | A61M 1/60 |
| 2024/0164937 A1 | 5/2024 | Gloeckner et al. | |
| 2024/0299205 A1 | 9/2024 | Hughett, Sr. | |

FOREIGN PATENT DOCUMENTS

| | | | |
|---|---|---|---|
| GB | 1422638 | A | 1/1976 |
| KR | 101901532 | B1 | 9/2018 |
| WO | 2002000148 | A2 | 1/2002 |
| WO | 2007050716 | A1 | 5/2007 |
| WO | 2019206941 | A1 | 10/2019 |
| WO | 2021211729 | A1 | 10/2021 |
| WO | 2022216507 | A1 | 10/2022 |
| WO | 2023244238 | A1 | 12/2023 |

OTHER PUBLICATIONS

Wolfram Mathworld Spherical Sector "https://web.archive.org/web/20180715224119/https://mathworld.wolfram.com/SphericalSector.html" Jul. 15, 2018 (Year: 2018).*

PCT/US2022/022669 filed Mar. 30, 2022 International Search Report and Written Opinion dated Jul. 15, 2022.

PCT/US2022/033886 filed Jun. 16, 2022 International Search Report and Written Opinion dated Jan. 19, 2023.

U.S. Appl. No. 17/528,037, filed Nov. 16, 2021 Final Office Action dated Jul. 10, 2023.

U.S. Appl. No. 17/528,037, filed Nov. 16, 2021 Non-Final Office Action dated Jan. 24, 2023.

U.S. Appl. No. 17/528,037, filed Nov. 16, 2021 Advisory Action dated Sep. 22, 2023.

U.S. Appl. No. 17/528,037, filed Nov. 16, 2021 Non-Final Office Action dated Nov. 8, 2023.

U.S. Appl. No. 17/528,037, filed Nov. 16, 2021 Final Office Action dated Feb. 15, 2024.

* cited by examiner

EXTERNAL FEMALE GRAVITY-BASED DRAINAGE

PRIORITY

This application claims the benefit of priority to U.S. Provisional Application No. 63/221,784, filed Jul. 14, 2021, which is incorporated by reference in its entirety into this application.

SUMMARY

Briefly summarized, embodiments disclosed herein are directed to an external, female, gravity-based drainage systems and associated methods thereof. Female patients with functional incontinence are aware of a need to urinate but may not have the means to get to a toilet in a timely manner. For example, the patient's conditions may include morbid obesity, severe arthritis, amputees, or the like. As such, embodiments disclosed herein allow the user to relieve themselves from either a standing, seated, or a recumbent position. Voided urine can be captured by the device and gravity-fed into a tubing and into a suitable collection container, urine bag, or toilet. Advantageously, embodiments, disclosed herein can be easily grasped on a single side by one or two digits, facilitating manipulation of the device, even by patients with reduced dexterity.

Disclosed herein is a drainage system including, a body defining a substantially spheroidal shape having a top side, a bottom side, a front side, a rear side, a left side and a right side, and having, a finger groove disposed in one of the front side, left side, or right side and extending vertically, and a funnel disposed on the rear side and extending to a spout disposed proximate a center point of the body, and a drainage tube defining a lumen and extending from a first end to a second end, the first end coupled to a bottom side of the body and in fluid communication with the spout.

In some embodiments, the finger groove defines one of a semi-circular, semi-elliptical, triangular or polygonal cross-sectional shape. In some embodiments, the body is configured to be grasped by the front side with one or more digits. In some embodiments, the funnel defines a spherical sector shape extending from a rear surface of the body towards the center point of the body. In some embodiments, a perimeter of the funnel defines a circular, elliptical, or vesica piscis shape. In some embodiments, the drainage tube includes a pleated section configured to articulate an axis of the drainage tube. In some embodiments, the body is formed of a compliant material including one of a plastic, polymer, elastomer, rubber, or silicone rubber.

In some embodiments, the body is formed of a rigid material and includes a compliant material disposed over a portion thereof, the compliant material including one of a plastic, polymer, elastomer, rubber, or silicone rubber. In some embodiments, an axis of the funnel extends at an angle relative to an axis of the drainage tube. In some embodiments, the funnel is configured to receive a labia region therein. In some embodiments, a second end of the drainage tube, opposite the first end, is coupled to a collection bag.

Also disclosed is a method of draining a fluid from a patient including, grasping a front side of a body of a drainage system, the body defining a substantially spheroidal shape and including a funnel disposed on a rear side, placing the funnel over a labia region of the patient, directing a fluid flow towards a funnel spout disposed proximate a center point of the body, and directing the fluid flow through a lumen of a drainage tube, the drainage tube coupled to a bottom surface of the body.

In some embodiments, a first end of the drainage tube is coupled to the body and a second end of the drainage tube, opposite the first end, is coupled to a collection bag. In some embodiments, the tube includes a pleated portion configured to articulate an axis of the tube. In some embodiments, grasping the front side of the body further includes placing a digit into a finger groove, the finger groove extending vertically across the front side of the body. In some embodiments, the finger groove includes one of a semi-circular, semi-elliptical, triangular or polygonal cross-sectional shape.

In some embodiments, the funnel defines a spherical sector shape extending from a rear surface of the body towards the center point of the body. In some embodiments, a perimeter of the funnel defines a circular, elliptical, or vesica piscis shape. In some embodiments, the body is formed of a compliant material including one of a plastic, polymer, elastomer, rubber, or silicone rubber. In some embodiments, the body is formed of a rigid material includes a compliant material disposed over a portion thereof, the compliant material including one of a plastic, polymer, elastomer, rubber, or silicone rubber. In some embodiments, an axis of the funnel extends at an angle relative to an axis of the drainage tube.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

Figure 1C:
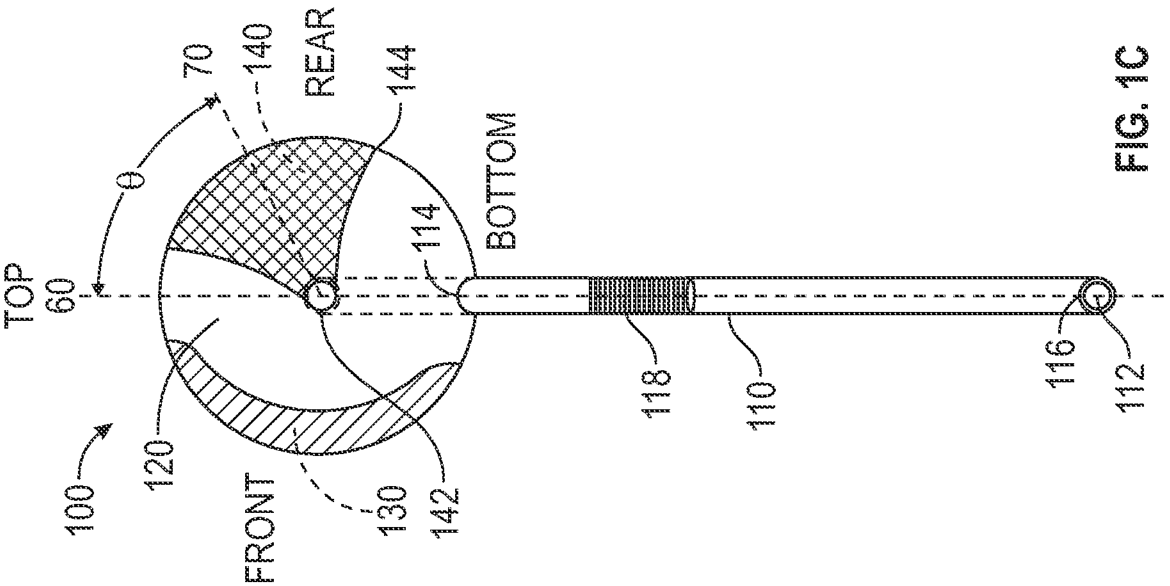
FIG. 1C shows a side view of an external gravity-based drainage system, in accordance with embodiments disclosed herein.
Figure 1B:
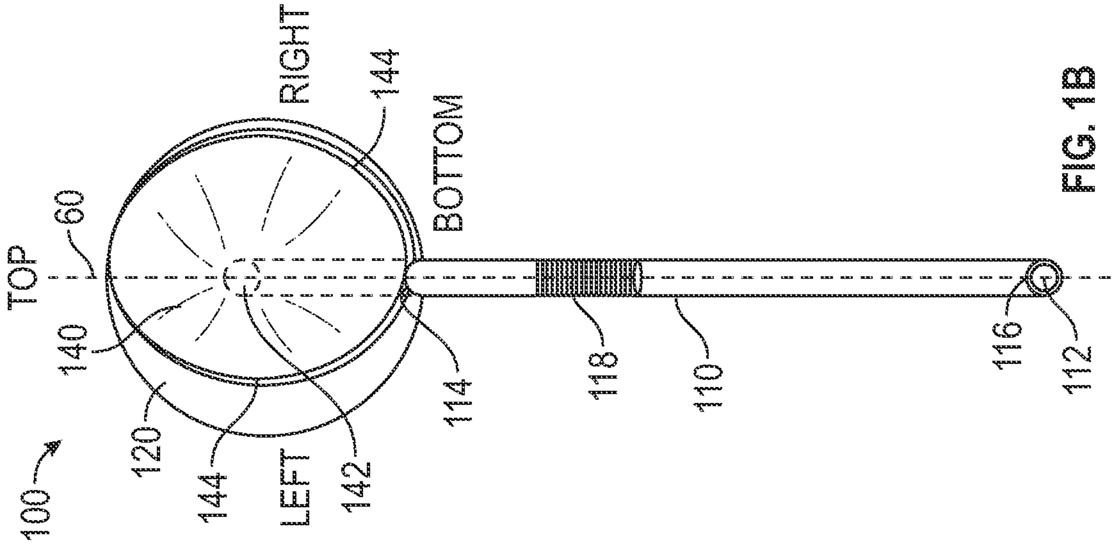
FIG. 1B shows a rear perspective view of an external gravity-based drainage system, in accordance with embodiments disclosed herein.
Figure 1A:
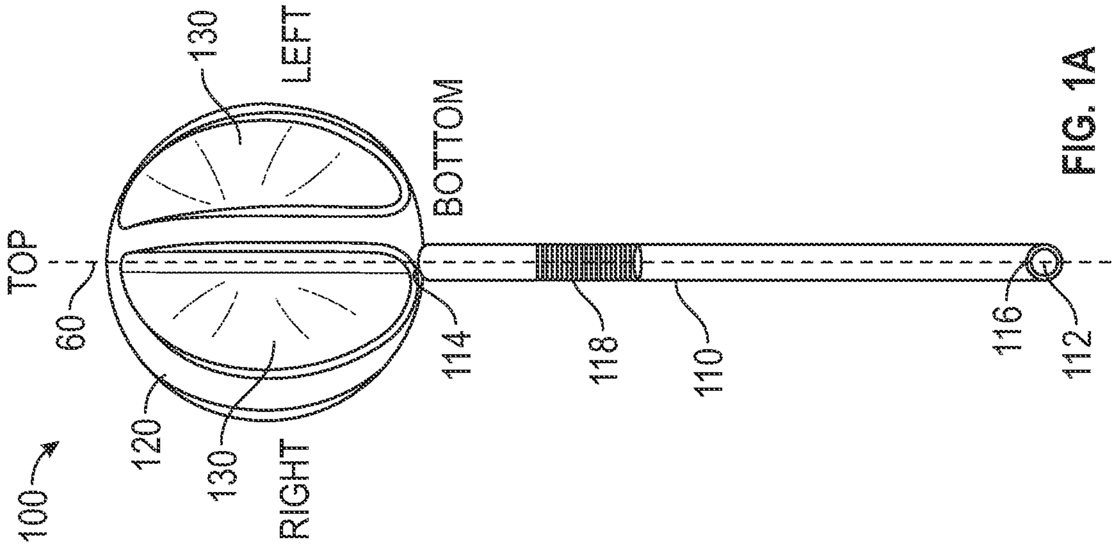
FIG. 1A shows a front perspective view of an external gravity-based drainage system, in accordance with embodiments disclosed herein.

To assist in the description of embodiments described herein, as shown in FIG. 1A, a longitudinal axis extends substantially parallel to an axial length of the catheter. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

FIGS. 1A-1C show various perspective views of an external gravity-based drainage system ("system") 100. The system 100 can generally include a drainage tube 110 in fluid communication with a body 120. The drainage tube 110 can define a lumen 112 extending from a first end 114 to a second end 116. The first end 114 can be coupled to the body 120 and provide fluid communication between the body 120 and the tube lumen 112. In an embodiment, the tube 110 can be integrally formed with the body 120. In an embodiment, the tube 110 can be coupled to the body using an interference fit, press-fit, snap-fit, or threaded engagement and can be selectively detachable from the body 120.

In an embodiment, the tube can be formed of a rigid or compliant material, such as a plastic, polymer, metal, alloy, composite, rubber, silicone rubber, combinations thereof, or the like. In an embodiment, the second end 116 of the tube 110 can be coupled to a collection container, collection bag, or the like. In an embodiment, the user can direct the second end 116 towards a suitable collection receptacle, toilet, or the like.

In an embodiment, a portion of the tube 110 can include a pleated section 118 configured to allow an axis of the tube 110 to articulate, similar to a concertina-style hinge. Advantageously, the pleated section 118 can allow a user to manipulate the tube 110 from a substantially linear configuration (i.e. extending vertically along an axis 60), to an angled configuration, angled relative to the vertical axis 60. Further, the tube 110 can remain in the angled configuration until manipulated to a different configuration. As such, the user can direct the second end 116 of the tube 110 towards a collection container, or the like, and the tube 110 can substantially remain in position until re-positioned by the user.

In an embodiment, the lumen 112 of the tube 110 can include a check valve, one way valve, or the like, configured to allow a fluid to flow in a first direction from the first end 114 to the second end 116 but can prevent a fluid flow in a second direction from the second end 116 to the first end 114. Advantageously, the check valve can prevent a fluid flowing from a portion of the tube lumen 112 and/or from a collection container towards the body 120 and into the funnel 140.

The body 120 can define a substantially spheroidal shape having a minimum diameter of between 2 cm and 10 cm. However smaller or larger diameters are also contemplated. As used herein, a "spheroidal" shape can include any spherical or ellipsoidal shape. For example, a ball shape, football/rugby ball (prolate spheroid) shape, egg shape, ovoidal shape, or the like. The first end 114 of the tube 110 can be coupled to a bottom surface of the body 120. A front side of the body 120 can include one or more finger grooves 130. The finger grooves 130 can define a linear or curvilinear channel extending substantially vertically from a top side to a bottom side. A rear side of the body 120 can include a funnel 140 extending from an outer surface of the body to a spout 142 that is in fluid communication with the drainage tube lumen 112.

Figure 2B:
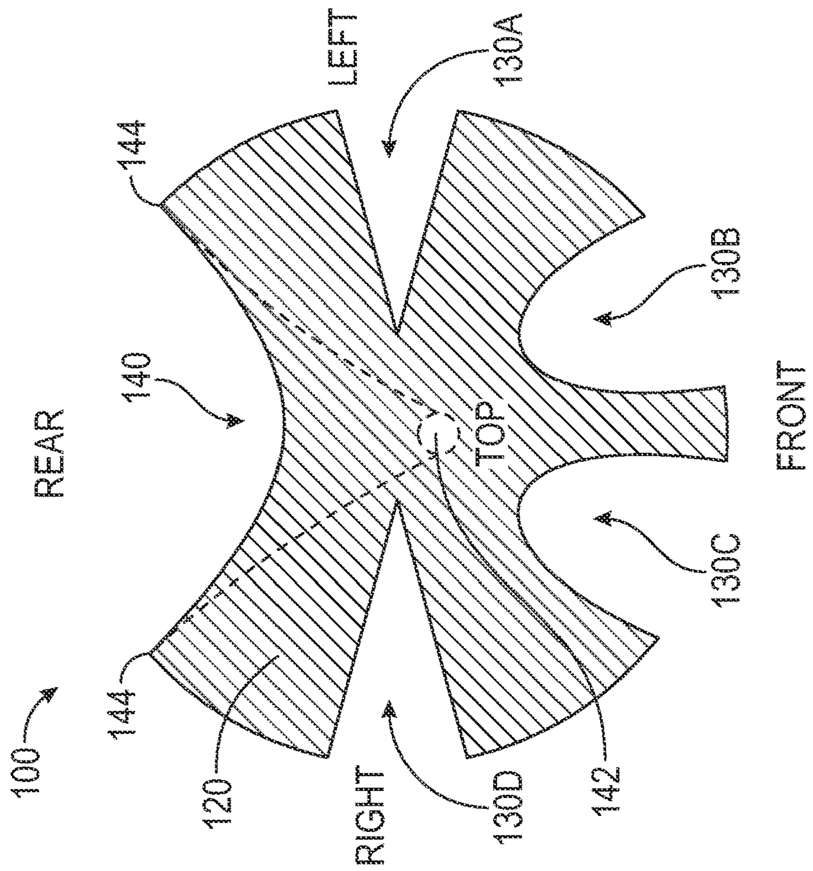
FIG. 2B shows a plan view of an external gravity-based drainage system, in accordance with embodiments disclosed herein.
Figure 2A:
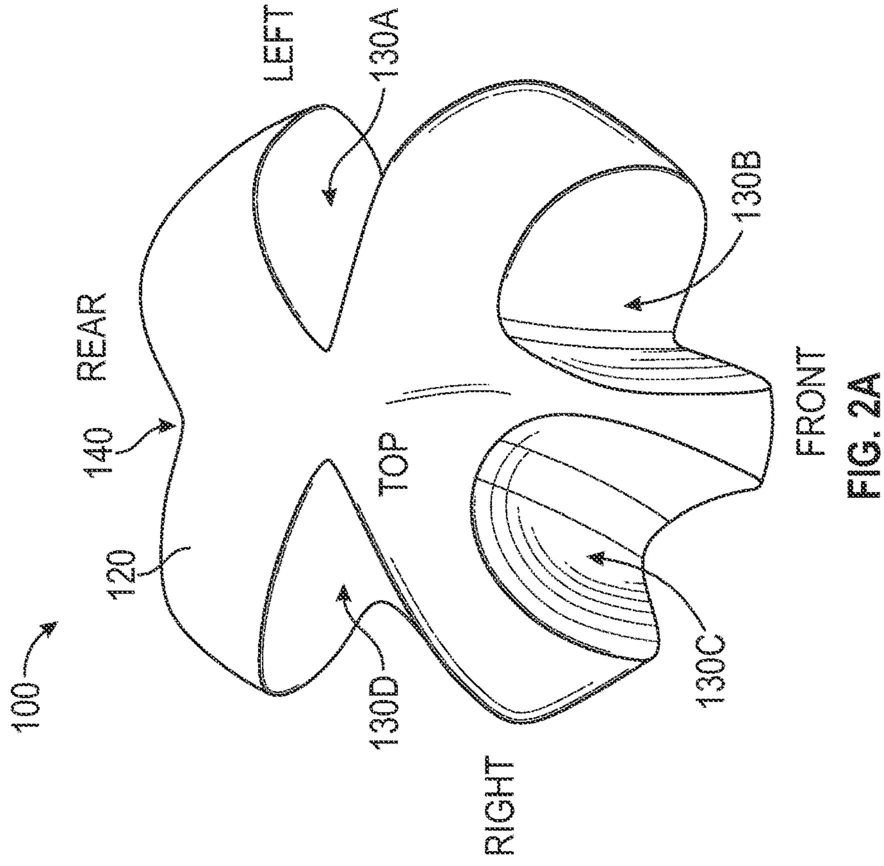
FIG. 2A shows a top side perspective view of an external gravity-based drainage system, in accordance with embodiments disclosed herein.

As shown in FIG. 2B, in an embodiment, one or more finger grooves 130 can define a semi-circular, or semi-elliptical cross-sectional shape, e.g. finger grooves 130B, 130C. A radius of curvature of the cross-sectional shape of the finger groove 130 can be substantially equal to that of a digit of a user. As such, the finger groove 130 can receive a digit of the user securely therein. Advantageously, the semi-circular, or semi-elliptical cross-sectional shape, with a radius of curvature similar to that of a digit of a user, provides a large contact area between the body 120 and the user's digit, providing improved grip therebetween.

In an embodiment, one or more finger grooves 130, e.g. finger grooves 130A, 130D, can define an angular cross-sectional shape, e.g. triangular. However it will be appreciated that other faceted, polygonal cross-sectional shapes are also contemplated. Advantageously, the angular cross-sectional shape of finger grooves 130A, 130D allow a user to "wedge" a digit into the groove 130 in an interference fit engagement, allowing a user to grip the body 120. Further, the "wedge" shaped finger groove 130 can securely engage digits of different sizes therein, providing increased versatility between different users.

Figure 3B:
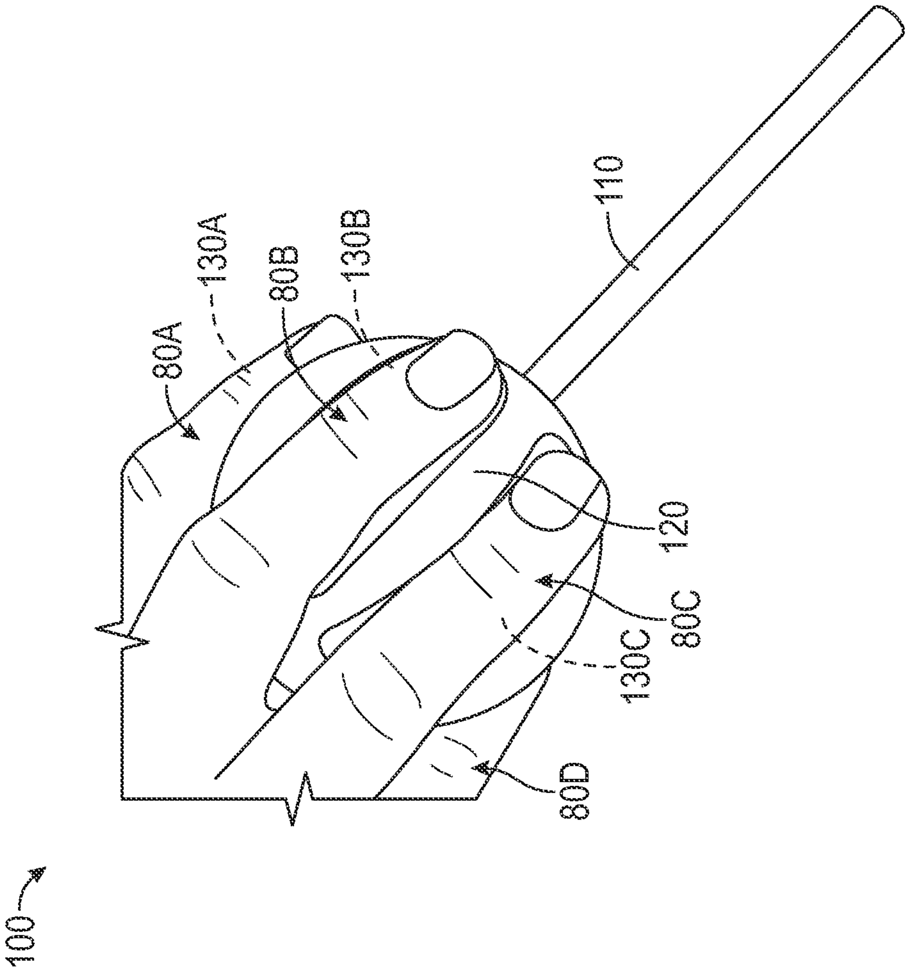
FIGS. 3A-3B show front views of an external gravity-based drainage system being held by a user, in accordance with embodiments disclosed herein.
Figure 3A:
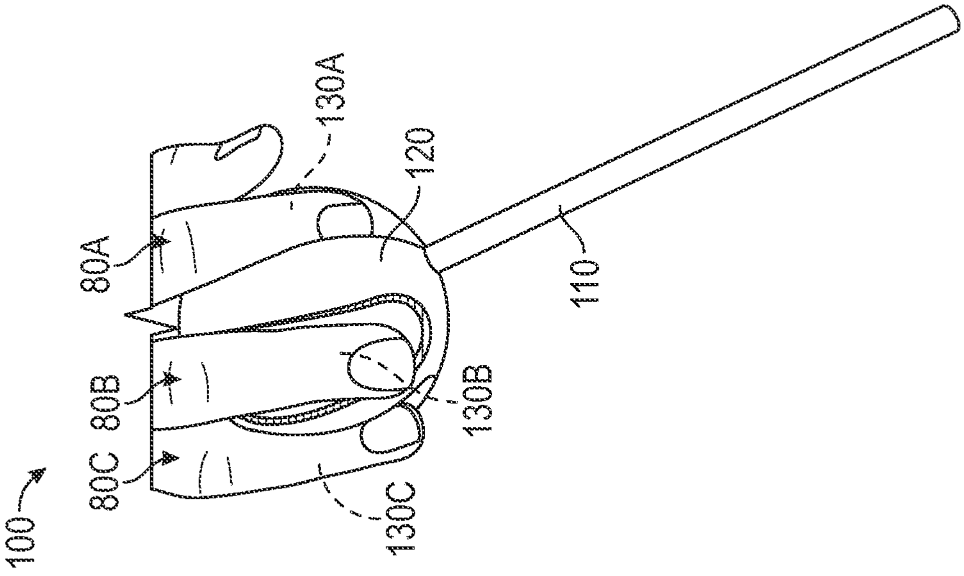
Figure 3C:
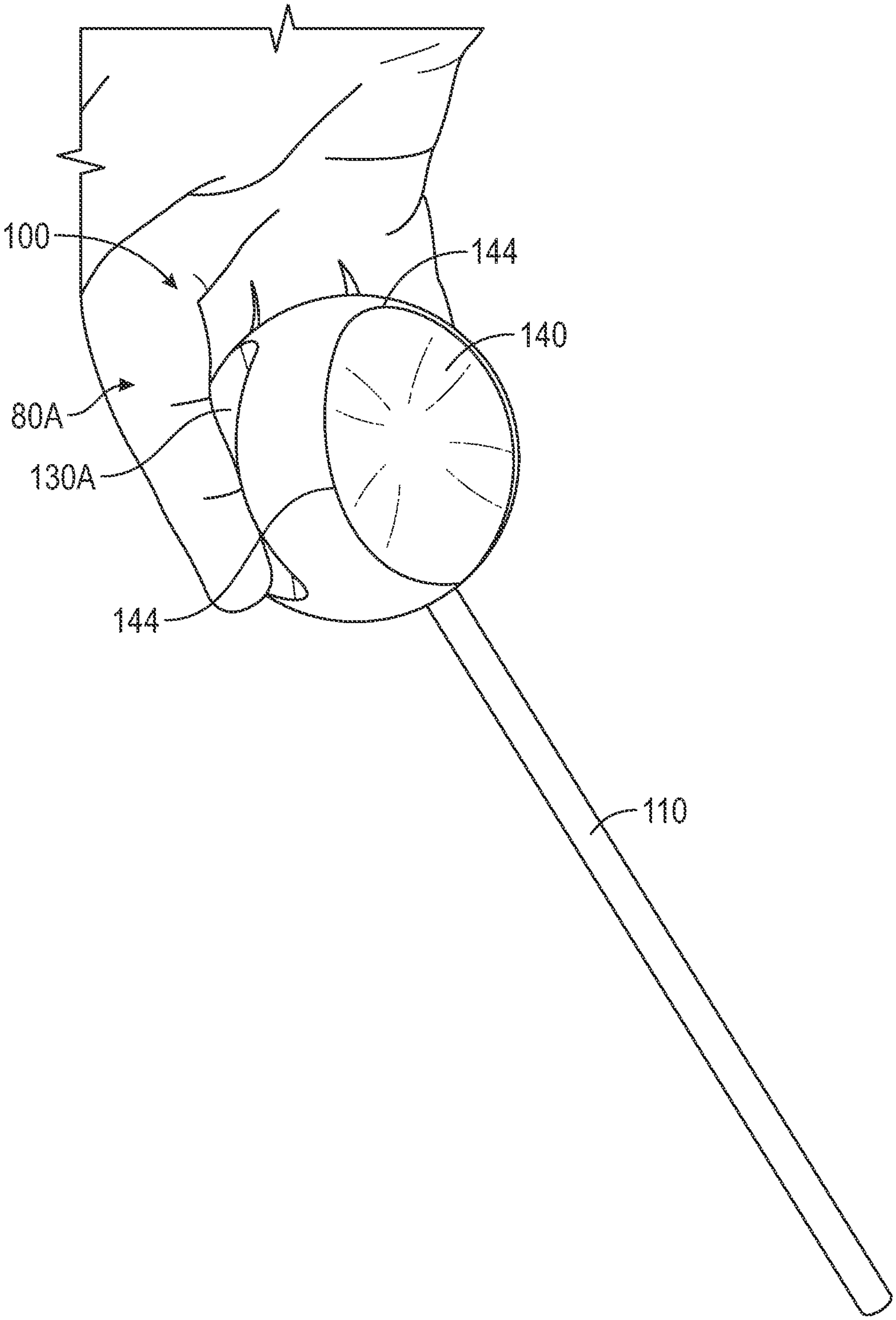
FIG. 3C shows a rear view of an external gravity-based drainage system being held by a user, in accordance with embodiments disclosed herein.

In an embodiment, as shown in FIGS. 3A-3C, the one or more finger grooves 130 can be configured to allow a user to grasp the body 120 substantially from a single side (i.e. the front side) without requiring any opposing force applied to an opposite side (i.e. from a thumb digit). Advantageously, this allows the user to position the body 120 within a groin region with one hand and without dropping the drainage system 100. More specifically, this allows a user to grasp a front side of the body 120 and position the funnel 140, disposed on a rear side, over a labia region to capture any fluids (e.g. urine) voided therefrom and direct the fluids into the drainage tube 110. This can be of particular importance for users with reduced dexterity where grasping and manipulating devices within the groin region can be challenging.

In an embodiment, the one or more finger grooves 130 can be configured to allow a user to grip the body 120 between two or more digits 80 without requiring an opposing force, e.g. from a thumb digit. For example, a user can place a first digit 80A into a first finger groove 130A and a second digit 80B into a second finger groove 130B and grasp a portion of the body 120 extending therebetween. In an embodiment, a third digit 80C can be placed into a third finger groove 130C and/or a fourth digit 80D can be placed into the fourth finger groove 130D, or combinations thereof, to further securely grasp the body 120. As will be appreciated, these combinations of digit(s) 80 and finger grooves 130 are exemplary and any combination of digits 80A-80D can be placed in any combination of finger grooves 130A-130D as desired by the user. In an embodiment, the one or more finger grooves 130 can be configured to allow a user to grip the body 120 with only a single digit 80.

In an embodiment, as shown in FIGS. 1B-1C, a rear side of the body 120, opposite the front side, can include a funnel 140. The funnel 140 can extend from a surface of the body 120 to a spout 142 disposed proximate a center point of the body. The spout 142 can be in fluid communication with the drainage tube lumen 112. An axis 70 of the funnel 140 can extend from the spout 142 to a surface of the body 120, i.e. substantially at a midpoint within the perimeter 144. In an embodiment, the axis 70 of the funnel 140 can extend at an angle (θ) relative to a vertical axis 60, substantially defined by the tube 110. In an embodiment, the angle (θ) can be between 40° and 160°. In an embodiment, the axis 70 of the funnel 140 can extend perpendicular relative to a vertical axis 60, substantially defined by the tube 110.

In an embodiment, the funnel 140 can define a spherical-sector shape or a lensed spherical-sector shape. Worded differently, when viewed from a left side view (FIG. 1C), the funnel can define a substantially spherical-sector shape extending from a rear surface of the body 120 to a spout 142. When viewed from a rear side view, a perimeter 144 of the funnel 140 can define either a spherical shape, an elliptical shape, or as shown in FIG. 1B a lensed, or vesica piscis, shape. Advantageously, the shape of the perimeter 144 of the funnel 140 can be configured to receive the labia region therein and can direct any fluids towards the spout 142 that is in fluid communication with the tube 110.

In an embodiment, the body 120 can be formed of a substantially rigid material such as a plastic, polymer, metal, alloy, composite, combinations thereof, or the like. In an embodiment, the body 120 can be formed of a compliant material such as a plastic, polymer, elastomer, composite, rubber, silicone rubber, combinations thereof, or the like. In an embodiment, the body 120 can include two or more materials displaying different mechanical properties. For example, the body 120 can be formed of a substantially rigid material and can include a second material, disposed thereon displaying more compliant, or elastically deformable, or malleable (plastically deformable) mechanical properties. For example, a finger groove 130 and/or a perimeter 144 of the funnel 140 can include a silicone rubber or similar compliant material. In an embodiment, the second material can display a relatively higher friction co-efficient. Advantageously, the second material can be more comfortable when placed against a skin surface. Advantageously, the second material can provide improved grip.

In an embodiment, the body 120 can be formed of an impervious material and/or display hydrophobic or super hydrophobic properties (e.g. hydrophobic coatings, super-hydrophobic coatings, nano structures, or the like). Advantageously, the impervious or hydrophobic properties allow the body 120 to be easily cleaned and readily direct fluids into the spout 142 and into the drainage tube 110. In an embodiment, the body 120 or portions thereof, can include an anti-bacterial coating disposed thereon to mitigate the formation of biofilms or similar pathogens.

Figure 4A:
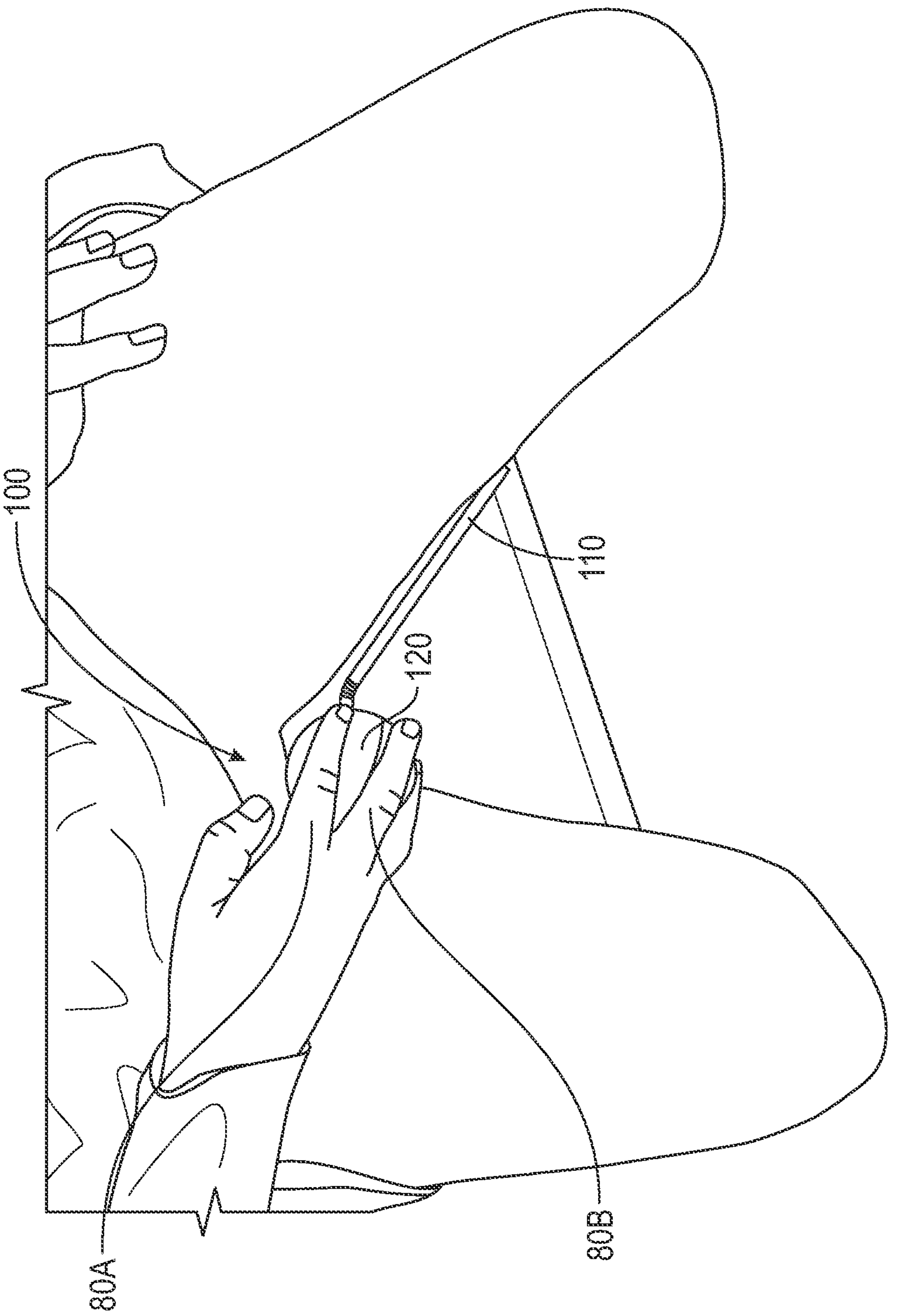
FIGS. 4A-4B show an exemplary method of use for an external gravity-based drainage system being held by a user, in accordance with embodiments disclosed herein.
Figure 4B:
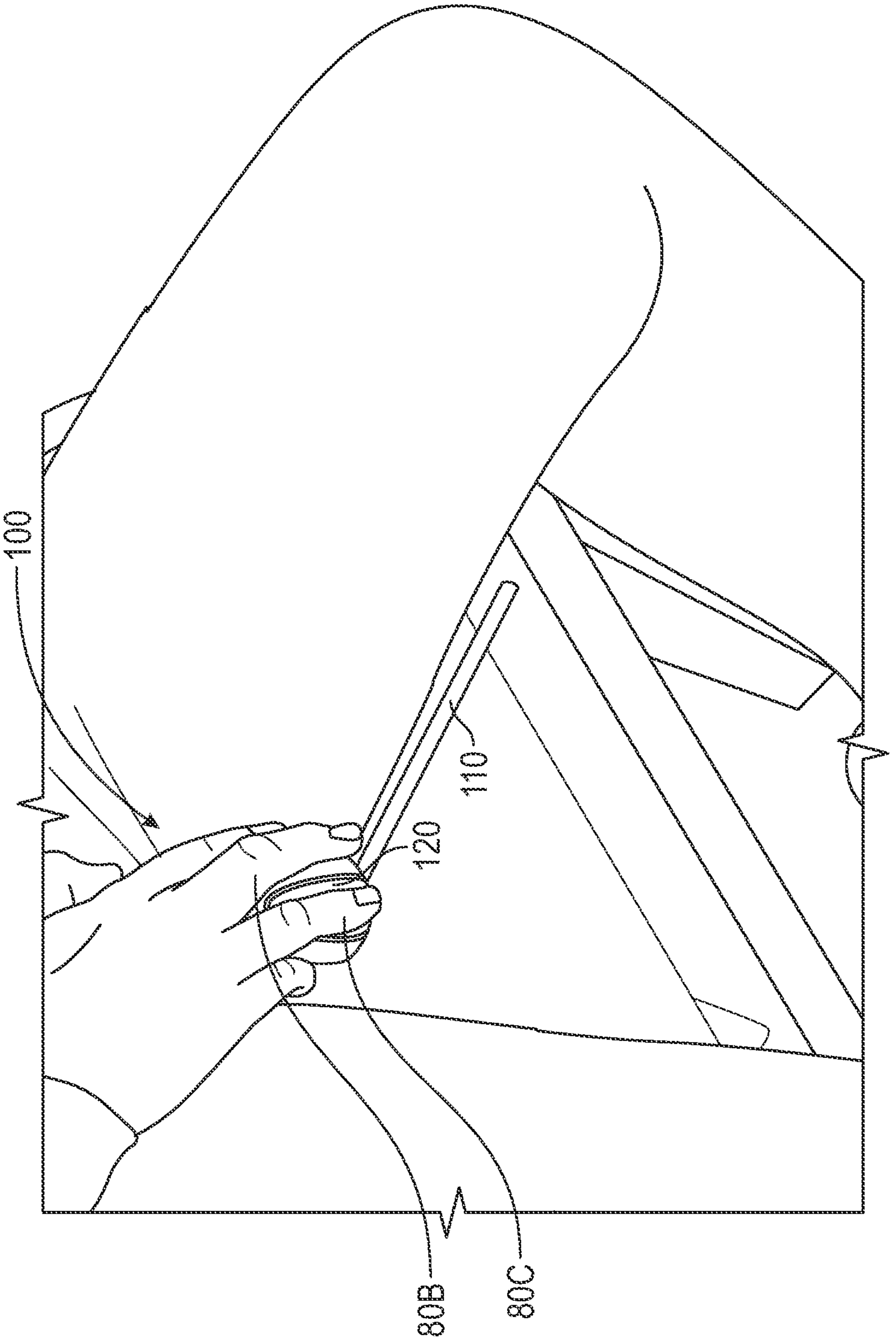

FIGS. 4A-4B show an exemplary method of use for the system 100. A user can grasp the body 120 from a front side, using one or more digits 80, as described herein. The user can then place a rear side of the body 120 into the groin region with the funnel 140 disposed over the labia region. The tube 110 can extend from a bottom surface of the body 120. In an embodiment, the user can direct a second end 116 of the tube towards a collection receptacle, container, toilet, urinal, or the like. In an embodiment, the pleated section 118 is configured to maintain the axis of the second end 116 relative to the body 120, when angled as such by the user. The angled drainage tube 110 can remain in place until repositioned by the user. In an embodiment, the tube can be in fluid communication with a collection bag, or the like disposed below the body 120. The user can then void the bladder, allowing fluids to be captured by the funnel 140 and directed into the funnel spout 142 and into the tube lumen 112 and optionally into a collection bag.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A drainage system, comprising:
- a gripping body, including:
  - at least three finger grooves including opposing wedge-shaped grooves configured to provide an interference fit engagement with a finger placed therein; and
  - a funnel configured for positioning over a labia region of a female patient, the funnel disposed on a rear side of the gripping body between the opposing wedge-shaped grooves; and
- a drainage tube in fluid communication with the funnel.

2. The drainage system according to claim 1, wherein the opposing wedge-shaped grooves have a triangular cross-sectional shape.

3. The drainage system according to claim 1, wherein the at least three finger grooves includes side-by-side grooves on a front side of the gripping body.

4. The drainage system according to claim 1, wherein the funnel defines a spherical sector shape.

5. The drainage system according to claim 1, wherein the gripping body defines a spheroidal shape.

6. The drainage system according to claim 1, wherein the drainage tube includes a pleated section configured to articulate an axis of the drainage tube.

7. The drainage system according to claim 1, wherein the gripping body is formed of a compliant material including one of a plastic, a polymer, an elastomer, a rubber, or a silicone rubber.

8. The drainage system according to claim 1, wherein the gripping body is formed of a rigid material and includes a compliant material disposed over a portion thereof, the compliant material including one of a plastic, a polymer, an elastomer, a rubber, or a silicone rubber.

9. The drainage system according to claim 1, wherein an axis of the funnel extends at an angle relative to an axis of the drainage tube.

10. The drainage system according to claim 1, wherein the funnel extends to a spout disposed proximate a center point of the gripping body.

11. The drainage system according to claim 1, wherein the drainage tube is coupled to a collection bag.

12. A method of using a drainage system, comprising:

grasping a gripping body of the drainage system, the gripping body comprising at least three finger grooves including opposing wedge-shaped grooves, the grasping including inserting a finger into each of the opposing wedge-shaped grooves, each finger engages the respective opposing wedge-shaped groove in an interference-fit engagement;

placing a funnel of the gripping body positioned between the opposing wedge-shaped grooves over a labia region; and urinating into the funnel.

13. The method according to claim 12, wherein a drainage tube is coupled to the gripping body and to a collection bag.

14. The method according to claim 13, wherein the drainage tube includes a pleated portion configured to articulate an axis of the drainage tube.

15. The method according to claim 12, wherein grasping the gripping body further includes placing two fingers in side-by-side grooves of the at least three finger grooves.

16. The method according to claim 15, wherein the opposing wedge-shaped grooves have a triangular cross-sectional shape.

17. The method according to claim 12, wherein the funnel defines a spherical sector shape.

18. The method according to claim 12, wherein the gripping body defines a spheroidal shape.

19. The method according to claim 12, wherein the gripping body is formed of a compliant material including one of a plastic, a polymer, an elastomer, a rubber, or a silicone rubber.

20. The method according to claim 12, wherein the gripping body is formed of a rigid material and includes a compliant material disposed over a portion thereof, the compliant material including one of a plastic, a polymer, an elastomer, a rubber, or a silicone rubber.

21. The method according to claim 12, wherein an axis of the funnel extends at an angle relative to an axis of a drainage tube in fluid communication with the funnel.

22. The drainage system according to claim 1, wherein a trough of a wedge-shaped groove of the opposing wedge-shaped grooves extends along a linear axis and wherein a first wall of the wedge-shaped groove extends from the trough at an angle of less than 45° relative to a second wall of the wedge-shaped groove extending from the trough.

23. The drainage system according to claim 1, wherein a trough axis of each finger groove of the at least three finger grooves extends parallel to each other.

24. The method according to claim 12, wherein a trough of a wedge-shaped groove of the opposing wedge-shaped grooves extends along a linear axis and wherein a first wall of the wedge-shaped groove extends from the trough at an angle of less than 45° relative to a second wall of the wedge-shaped groove extending from the trough.

25. The method according to claim 12, wherein a trough axis of each finger groove of the at least three finger grooves extends parallel to each other.

* * * * *